United States Patent [19]

Schneider et al.

[11] 4,043,989

[45] Aug. 23, 1977

[54] OXAZEPAM DERIVATIVES FOR IMMUNOASSAY REAGENTS

[75] Inventors: Richard S. Schneider, Saratoga, Calif.; Steven J. Gould, South Windham, Conn.

[73] Assignee: Syva Company, Palo Alto, Calif.

[21] Appl. No.: 612,425

[22] Filed: Sept. 11, 1975

[51] Int. Cl.² ................................................ C07G 7/00
[52] U.S. Cl. .......................... 260/112 R; 260/112.5 R; 260/121; 260/239.3 D; 424/85; 424/88
[58] Field of Search .................. 260/112 R, 121, 117, 260/239.3 D, 112.5; 424/85, 88

[56] References Cited

U.S. PATENT DOCUMENTS

| | | | |
|---|---|---|---|
| 3,520,877 | 7/1970 | Fryer | 260/239.3 D |
| 3,671,518 | 6/1972 | Hellerbach | 260/239.3 D |
| 3,799,920 | 3/1974 | Ferrari | 260/239.3 D |
| 3,801,568 | 4/1974 | Nudelman | 260/239.3 D |
| 3,825,533 | 7/1974 | Nudelman | 260/239.3 D |

*Primary Examiner*—Paul R. Michl
*Attorney, Agent, or Firm*—Townsend and Townsend

[57] ABSTRACT

Compounds are provided for use in the preparation of reagents which can be used in immunoassays for benzdiazepines, particularly as their urinary metabolites. The compounds are non-oxo-carbonyl derivatives conjugated to the 3-position of the benzdiazepine, which in turn are conjugated to antigenic polypeptides for formation of antibodies for use in immunoassays. The antibodies produced, when employed in immunoassays, are found to be able to detect the ingestion of a wide variety of benzdiazepine drugs as determined by positive results with the urine of the patient.

6 Claims; No Drawings

OXAZEPAM DERIVATIVES FOR IMMUNOASSAY REAGENTS

BACKGROUND OF THE INVENTION

1. Field of the Invention

Tranquilizers have become more and more popularly employed in the treatment of anxiety. Due to the effectiveness of this class of drugs, there has become an increasing availability of drugs and their use has become abused. In non-therapeutic treatments, relatively higher levels of the drugs may be employed. It has therefore become a matter of some importance that economical and rapid means for the determination of the presence of the drug in urine or other body fluid be established.

There are a number of different ways for detecting the presence of a drug in urine. Some of these techniques employ chromatographic techniques such as vapor phase chromatography, thin-layer chromatography, and the like. These techniques depend upon the properties of adsorption of the drug of interest, which allow for the drug to be separated from other materials in the sample being tested. Another group of techniques rely on the ability of a receptor such as an antibody, to distinguish the molecule of interest from other molecules which may be present. These techniques are referred to as immunoassays since they depend on a mammalian immunological response for the production of the antibodies which recognize the compound of interest.

In producing antibodies, one normally conjugates a molecule which resembles the compound of interest to a large molecule which is antigenic. The resulting conjugate is then injected into an animal, normally a domestic animal, to elicit an immunological response with the production of antibodies which recognize the compound of interest.

In producing antibodies, there are a number of considerations as to the usefulness of the antibody composition in an immunoassay. The concentration of useful antibodies must be sufficiently high, so that upon dilution in the assay, there is sufficient antibody to provide for the necessary sensitivity. The binding constant of the antibody should also be high, so that large concentrations of antibodies are not required to ensure a reasonable amount of binding of any of the compound present to the antibody. It should be recognized that normally the concentrations of interest are only a few micrograms per milliliter or less so that one is dealing with extremely small amounts of the compound being assayed.

There is also concern about the degree of specificity for the antibody. Where there are a class of drugs having similar structure and similar properties and the intent is to determine whether any of these drugs are being abused, it is desirable that the antibody be able to detect the metabolites of as many of the class of drugs as possible. That is, the antibody should have reasonably good binding to all of the metabolites, so that concentrations normally encountered in urines with persons using non-therapeutic dosages will give a positive result. With the benzdiazepines, the drugs of interest include diazepam, oxazepam, medazepam, temazepam, des-N-methyl diazepam and chlordiazepoxide.

2. Description of the Prior Art

U.S. Pat. No. 3,817,837 describes a homogeneous enzyme immunoassay technique, as well as enzyme conjugates for use in the assay. Included among potential conjugates are benzdiazepine derivatives. U.S. Pat. No. 3,609,834 describes a homogeneous spin labeled immunoassay, employing a free radical detector. Included among potential reagents are spin labeled benzdiazepine.

SUMMARY OF THE INVENTION

Compounds are provided for conjugation to antigens for the production of antibodies which recognize benzdiazepine urinary metabolites, as well as for conjugation to detector molecules to stable free radicals and enzymes for use as reagents in immunoassays. The 3-position of a 5-phenyl-7-chloro[6,7]benzdiazepine is used as the site for providing a non-oxo-carbonyl functionality for conjugation to a polypeptide antigen. The resulting conjugated antigen is employed for the production of antibodies by known ways, which are found to be highly specific for urinary metabolites of a wide variety of benzdiazepine drugs.

DESCRIPTION OF THE SPECIFIC EMBODIMENTS

Novel compounds are provided which are used in the formation of reagents in immunoassays. The compounds are primarily 5-phenyl-7-chloro-3H[6,7]benzo-1,4-diazepines bonded at the 3-position to a non-oxo-carbonyl group, which in turn is employed for conjugation to polypeptides in proteins. (For the purpose of this invention, non-oxo-carbonyl will include the thiono and imido, sulfur and nitrogen analogs, unless indicated otherwise.) The chain between the annular carbon atom and the non-oxo-carbonyl group will be relatively short, generally being at least one and not more than about 10, normally aliphatic, and may have one or more heteroatoms in the chain, as well as one or more functionalities along the chain, particularly non-oxo-carbonyl, more particularly oxygen non-oxo-carbonyl.

The non-oxo-carbonyl compounds of this invention will normally have from about 17 to 30 carbon atoms, more usually from about 18 to 26 carbon atoms.

For the most part, the compounds of this invention will have the following formula:

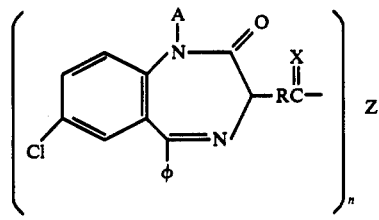

wherein:

R is a linking group, preferably an aliphatic linking group, of from 1 to 8 carbon atoms and 0 to 4 heteroatoms (chalcogen and nitrogen), preferably oxygen, particularly as oxy and non-oxo-carbonyl, more preferably 1 to 2 oxygen atoms and may be branched chain or straight chain, preferably straight chain having from 0 to 1 site of ethylenic unsaturation as the only aliphatic unsaturation, any nitrogen being present as tertiary amino or imido and any sulfur being present as thio;

A is hydrogen or lower alkyl of from 1 to 3 carbon atoms, particularly methyl, preferably hydrogen;

X is oxygen, sulfur or nitrogen, preferably oxygen;

Z is hydroxyl, alkoxyl of from 1 to 6 carbon atoms, more usually of from 1 to 3 carbon atoms, alkyl carbonate (OCO₂T¹, wherein T¹ is alkyl of from 1 to 6 carbon atoms, more usually 1 to 4 carbon atoms), Y wherein Y is a poly(amino acid), e.g. polypeptide residue (including polypeptides subunits of proteins); and

*n* is one except when Z is Y, when *n* will be equal to the number of acyl groups bonded to the amino groups of Z, and will be at least one, and not greater than the number of the amino functional groups available for bonding, usually not more than the molecular weight of Y divided by 500, more usually not more than the molecular weight of Y divided by 1500, and usually at least one per 50,000 molecular weight.

Preferred R groups include alkylene, alkenylene, oxycarbonylalkyl, N-lower alkyl (1–3 carbon atoms) oxycarbonylalkylaminoalkyl, oxycarbonylalkylthioalkyl, oxyalkyl, oxycarbonylalkenyl, and oxyalkenyl.

Illustrative R groups include:

| | |
|---|---|
| —OCO— | —OCOCH₂OCH₂— |
| —OCH₂CH=CH— | —OCH₂CH₂N(Me)CH₂— |
| —OCOCH₂CH₂CH₂— | —OCH₂CONHCH₂— |
| —OCOCH₂N(Me)CH₂— | —OCO(CH₂)₄— |
| —CH₂CH=CH— | —OCH₂— |

Preferred compounds of this invention will have the following formula:

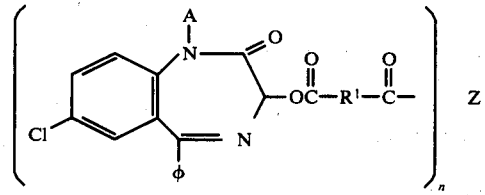

wherein:

A, Z, and *n* have been defined previously; and

R¹ is a bond or an aliphatic radical of from 1 to 6 carbon atoms, more usually of from 1 to 4 carbon atoms having from 0 to 1 site of ethylenic unsaturation as the only unsaturation, and from 0 to 1 heteroatom which is oxygen or nitrogen (atomic number 7–8), particularly oxygen as oxy in the chain, and may be branched or straight chained, preferably straight chained, i.e. polymethylene of from 2 to 4 carbon atoms.

The carboxylic acid and ester (Z = OW) will for the most part have the following formula:

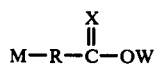

wherein:

R and X have been defined previously, but R is preferably OCOR¹ and X is preferably oxygen;

M is of the formula:

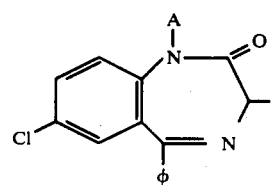

wherein:

A has been defined previously and is preferably hydrogen; and

W is hydrogen or alkyl of from 1 to 6, usually 1 to 4 carbon atoms.

Of particular interest are compounds where the non-oxo-carbonyl group is bonded to an amino group, which is part of a polypeptide or protein structure. One group of polypeptides and proteins is antigenic, so that by bonding the non-oxo-carbonyl derivatized benzdiazepine to the polypeptide or protein, antibodies can be formed to benzdiazepine. A narrower class of proteins, which also can be used as antigens, but will not normally be used as such, are enzymes which are employed as the detector in an immunoassay system. As antigens, inactive enzymes can be used.

Polypeptides usually encompass from about 2 to 100 amino acid units (usually less than about 12,000 molecular weight). Larger polypeptides are arbitrarily called proteins. Proteins are usually composed of from 1 to 20 polypeptide chains called subunits, which are associated by covalent or noncovalent bonds. Subunits are normally of from about 100 to 300 amino acid groups (or 10,000 to 35,000 molecular weight). For the purposes of this invention, polypeptide is intended to include individual polypeptide units and polypeptides which are subunits of proteins, whether composed solely of polypeptide units or polypeptide units in combination with other functional groups, such as porphyrins, as in haemoglobin or cytochrome oxidase.

The number of benzdiazepine groups will vary depending on whether the polypeptide is an enzyme or antigen. The maximum number of groups will be limited by the effect of substitution on solubility, activity, and the like. For the formation of antibodies, a sufficient number of benzdiazepine groups should be present, so as to provide a satisfactory harvest of antibodies to the benzdiazepines. Otherwise, the proportion of antibodies to benzdiazepines as compared to other compounds may be undesirably low.

The first group of protein materials or polypeptides which will be considered are the antigenic polypeptides. These may be joined to the non-oxo-carbonyl group of the benzdiazepine analog through an amino group. The amide product can be used for the formation of antibodies to benzdiazepines. The protein materials which may be used will vary widely, and will normally be from 1,000 to 10 million molecular weight, more usually 20,000 to 500,000 molecular weight.

With the antigens, there will be no more than one benzdiazepine group per 500, more usually 1,000, molecular weight, generally no more than one benzdiazepine group per 2,000 molecular weight, and not less than one benzdiazepine group per 100,000 molecular weight, usually not less than one benzdiazepine group per 50,000 molecular weight. With intermediate molecular weight antigens, those having molecular weights in the range of 20,000 to 1,000,000, the number of benzdiazepine groups will generally be from about 2 to 250, usually from 4 to 100. Low molecular weight antigens (1,000 to 5,000 molecular weight) may have 1 to 10, usually 2 to 5 benzdiazepine groups, so that there may frequently be as many as one benzdiazepine group per 500 molecular weight.

Enzymes will normally be of molecular weights in the range of about 10,000 to 600,000, usually in the range of about 12,000 to 150,000, and more usually in the range of 12,000 to 80,000. Some enzymes will have a plurality of enzyme subunits. It is intended, when speaking of enzyme molecular weights, to refer to the entire enzyme. There will be on the average at least about one benzdiazepine per enzyme, usually at least about two benzdiazepines per enzyme when the labeling is not limited to a specific amino group, and rarely more than 40 benzdiazepines per enzyme, usually not more than 30 benzdiazepines per enzymes. For example, with lysozyme the average number of benzdiazepine groups will be in the range of about 2 to 4.

While the benzdiazepine analog may be bonded through the non-oxo-carbonyl group to hydroxyl or mercapto groups, which are present in the proteins, for the most part the bonding will be to amino. Therefore, the compounds are described as amides, although esters and thioesters may also be present.

Amino acids present in proteins which have free amino groups for bonding to the carboxy modified benzdiazepine include lysine, arginine, ornithine, etc. The hydroxyl and mercaptan containing amino acids include serine, cysteine, and threonine.

Various protein and polypeptide types may be employed as the antigenic material. These types include albumins, enzymes, serum proteins, e.g. globulins, ocular lens proteins, lipoproteins, etc. Illustrative proteins include bovine serum albumin, keyhole limpet hemocyanin, egg albumin, bovine gamma-globulin, etc. Small neutral polypeptides which are immunogenic such as gramicidins may also be employed. Various synthetic polypeptides may be employed, such as polymers of lysine, glutamic acid, phenylalanine, tryosine, etc., either by themselves or in combination. Of particular interest is polylysine or a combination of lysine and glutamic acid. Any synthetic polypeptide must contain a sufficient number of free amino groups as, for example, provided by lysine.

The second group of protein molecules are the detectors. These are the enzymes to which the non-oxo-carbonyl modified benzdiazepines may be conjugated. As indicated, the benzdiazepine modified enzyme is useful for immunoassays. A description of the immunoassay technique will follow.

Various enzymes may be used such as peptidases, esterases, amidases, phosphorylases, carbohydrases, oxidases, reductaces, and the like. Of particular interest are such enzymes as lysozyme, peroxidase, α-amylase, dehydrogenases, particularly malate dehydrogenase and glucose-6-phosphate dehydrogenase, alkaline phosphatase, β-glucuronidase, cellulase and phospholipase. In accordance with the I.U.B. Classification, the enzymes of interest are: 1. Oxidoreductases, particularly Groups 1.1, and more particularly 1.1.1, and 1.11, more particularly, 1.11.1; and 3. Hydrolases, particularly 3.2, and more particularly 3.2.1.

The substituted proteins will for the most part have the following formula:

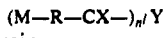

wherein:

Y is a polypeptide residue usually antigenic;

R has been defined previously, and is preferably —O—COR$^1$—;

M and X have been defined previously; and $n'$ will usually be of from 1 to 50, more usually from 2 to 35, when Y' is an enzyme residue. When Y' is an antigenic protein residue, $n'$ will usually range from the molecular weight of the protein divided by about 1,000, usually 1,500 to about 50,000. For small polypeptides, $n'$ will usually range from 1 to the molecular weight of the polypeptide divided by 500. For antigenic proteins of from 20,000 molecular weight to 1,000,000 molecular weight, $n'$ will generally average from 2 to 250.

Instead of an enzyme a stable free radical may be employed as the functionality for detection in the immunoassay. The stable free radicals are cyclic nitroxides having the nitrogen of the nitroxide as an annular member and from 0 to 1 other heteroatoms, i.e. oxygen and nitrogen, as annular members. The stable free radical molecules bonded to the non-oxo-carbonyl of the benziazepine derivatives will normally be from 7 to 16 carbon atoms, more usually from 7 to 12 carbon atoms. The amino functionality may be bonded directly to the annular carbon atom or may be bonded to the ring through an aliphatic chain of from 1 to 4 carbon atoms, more usually of from 1 to 2 carbon atoms. The molecules may have from 0 to 2 sites of ethylenic unsaturation, more usually from 0 to 1 site of ethylenic unsaturation.

For the most part, the stable nitroxide functionalities bonded to the non-oxo-carbonyl of the derivatized benzdiazepine will have the following formula:

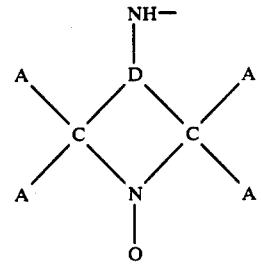

wherein:

D is a divalent aliphatic radical usually aliphatically saturated of from 1 to 6 carbon atoms, more usually of from 1 to 3 carbon atoms, only from 1 to 3, usually 2 to 3 of the carbon atoms in D being annular atoms; and A is lower alkyl (1 to 6, usually 1 to 3 carbon atoms), particularly methyl.

For the most part, compounds are pyrrolidine or piperidine derivatives, and D is hydrocarbon.

In forming the various amide products which find use in the subject invention, the carboxylic acid will normally be activated. This can be achieved in a number of ways. Two ways of particular interest are the reaction with a carbodiimide, usually a water soluble dialiphatic or dicycloaliphatic carbodiimide in an inert polar solvent, e.g. dimethylformamide, acetonitrile and hexamethylphosphoramide. The reaction is carried out by bringing the various reagents together under mild conditions and allowing sufficient time for the reaction to occur.

A second method is to form a mixed anhydride employing an alkyl chloroformate, e.g. isobutyl chloroformate. The mixed anhydride is formed by combining the carboxy substituted benzdiazepine, the alkyl chloroformate and the tertiary amine. The temperature is normally below ambient temperature.

At least a stoichiometric amount of the chloroformate is employed based on the benzdiazepine derivative, and usually an excess. The excess does not usually exceed three times stoichiometric. The tertiary amine is present in at least equimolar amounts to the chloroformate.

The mixture is then combined with the amino compound to be conjugated and the reaction allowed to proceed under mild conditions.

Also, esters of the carboxy modified benzdiazepine can be employed which are operative in water for acylating amine functions. As illustrative hydroxylic group is p-nitrophenol which can be used to prepare the p-nitrophenyl ester.

Finally, imidate esters may be employed under mild conditions at neutral or mildly basic pH in aqueous solvent systems.

The antibodies which are prepared in response to the conjugated antigens of this invention have strong specific binding to the parent drug, the conjugated antigen, the compound or derivative thereof used to conjugate to the antigen, the acid labeled compounds, e.g. enzyme conjugate and spin label conjugate.

EXPERIMENTAL (The following examples are offered by way of illustration and not by way of limitation. All temperatures not indicated are in Centigrade.)

EXAMPLE 1

Oxazepam Hemi-succinate

Oxazepam (2g, 7mmole) and succinic anhydride (1.2g and 11.2mmole) in pyridine (40ml, dried over barium oxide) were heated under a nitrogen atmosphere at 95° for 7 hours. The mixture was cooled, and the pyridine removed at reduced pressure. The residue was taken up in ethyl acetate and extracted into aqueous potassium carbonate, pH 13. After neutralizing the basic extracts with aqueous acid, the hemi-succinate was extracted into ethyl acetate, and the extracts washed with saturated brine. They were then dried, filtered, and concentrated in vacuo to give 2.1g (78%) of the crystalline hemi-succinate, which was recrystallized from ethyl acetate-cyclohexane: m.p. 204°–206° (lit. 204.5°–205.5°).

EXAMPLE 2

Oxazepam Hemi-succinate/BSA Conjugate

Oxazepam hemi-succinate (250mg, 0.65mmole) dissolved in dimethylformamide (3.7ml, dried over molecular seives) and cooled to −15° under a nitrogen atmosphere, was treated successively with triethylamine (72mg, 0.71mmole) and isobutylchloroformate (98mg, 0.71mmole). After 2 hours, the mixture was added dropwise to a solution of bovine serum albumin (BSA) (735mg) in distilled water (150ml) at 0°. The pH was maintained at 9.5 with 0.05N sodium hydroxide. After 3 hours, sodium bicarbonate (500mg) was added and the mixture stirred in the cold overnight. 1N Hydrochloric acid was added to reach pH 7.0, the mixture centrifuged at 12,000 rpm for 10 minutes, and the supernatant dialyzed against water. Lyophilization of the dialysate gave 700mg of the conjugate, whose hapten number was found by UV (max at 343nm) to be 17.5.

EXAMPLE 3

Oxazepam Hemi-succinate Spin-Label

The isobuyl mixed anhydride of oxazepam hemi-succinate (250mg, 0.65mmole) was prepared as described previously. To this was added 2,2,5,5-tetramethyl-3-amino-1-oxylpyrrolidine (100mg, 0.71mmole) in dimethylformamide (2ml), and after one hour, the mixture was allowed to warm to room temperature. A few hours later it was poured into water and adjusted to pH 9 with aqueous potassium carbonate. Extraction with methylene chloride and usual work-up of the extracts gave a gum from which the desired yellow, crystalline spin-label (190mg, 58%) was obtained by preparative tlc (one elution with 50% ethyl-methylene chloride and one elution with 6% methanol-chloroform).

EXAMPLE 4

Oxazepam Hemi-succinate Conjugate to Lysozyme

Into a reaction flask was introduced 20.4mg (5.04 × $10^{-2}$ mmoles) of oxazepam hemi-succinate, 1ml dimethylformamide, and 15µl of triethylamine and the mixture cooled to −15°. Isobutyl chloroformate (6.94µl, 5.3 × $10^{-2}$ mmoles ) is added, the mixture stirred for 45 minutes, while the temperature is allowed to rise to −5°.

This mixture is then added to a solution of 120mg (0.84 × $10^{-2}$ mmoles) of lysozyme in 10ml water, pH 8.7, at 4°, the pH being adjusted with 0.05N sodium hydroxide. During the addition the pH is maintained at 8.7 and the reaction allowed to continue until the pH is constant for about 30 minutes. The pH is then adjusted to 7.0, the product centrifuged and dialyzed against pH 6.0 0.025M Trismaleate buffer.

Antibodies were prepared employing the conjugate of Example 2 in accordance with known procedures. Sheep were injected with 1ml of a solution of 30mg/ml of the conjugate in 4 sites, with complete Freund's adjuvant and the injections repeated approximately on a monthly basis using incomplete Freund's adjuvant, with bleeds carried out one week after injection. The second bleed was harvested and the antibodies isolated according to known techniques.

The following is the procedure employed for the determination of the presence of Librium, Valium, and Oxazepam.

In carrying out the assay, a number of reagent solutions are prepared:

A. Buffer solution: Tris-maleate, 0.55M, pH 6.0;

B. Bovine serum albumin solution: 0.1 weight percent BSA in Tris-maleate prepared above;

C. Bacteria: 40mg of M. luteus suspended in 50ml buffer solution. The suspension is prepared daily, twelve hours before use and stored at 4° C;

D. Benzdiazepine-lysozyme (Example 4): the stock solution of benzdiazepine conjugated with lysozyme is diluted with 0.1 weight percent BSA and Tris-Maleate (0.025M Tris; pH 6.0) and stored.

The active lysozyme content of the working solution is determined by measuring at 436nm the rate of bacteriolysis at 30°. The assay solution is prepared by mixing 0.2mg bacteria, 0.02ml of 0.1 weight percent BSA-buffer, 0.08 ml synthetic urine (or urine where appropriate) and 0.50ml of the lysozyme solution. The antibody is employed in 0.025M Tris-maleate (pH 7.4) at a concentration suitable for 20µl to inhibit >85 percent of the benzdiazepine-lysozyme activity of the stock enzyme solution. The stock enzyme solution should provide about 150 OD units from a sample having no benzdiazepine to a sample where the benzdiazepine saturates the available antibody binding sites. (OD units are optical density units on a U.V. spectrometer at the measurement temperature.)

To prepare synthetic urine, 5.2g potassium chloride, 8.2g sodium chloride, 1.4g sodium dihydrogenphosphate, 1.4g disodium monohydrogenphosphate, and 11g of urea are combined in one liter of distilled water.

In carrying out the assay, 20µl of the antibody solution is added to 0.2ml of the bacterial suspension. To this solution is added 80µl of urine and the mixture diluted with one-half ml of the enzyme solution. The mixture is then aspirated into the spectrometer and the decrease in optical density is measured at 435nm for 40 seconds. The concentration of benzdiazepine in the urine sample is read from a standard curve prepared by using standardized solutions and taking readings.

To demonstrate the sensitivity of the antibodies produced in accordance with this invention, a wide variety of drugs were dissolved in synthetic urine and the concentration required to give the same result as oxazepam in the subject assay determined. The following table indicates the results.

| Compound | Level Equal to 1μg/ml Oxazepam μg/ml |
|---|---|
| Oxazepam | 1.0 |
| Des N-methyl diazepam | 0.6 |
| diazepam (Valium®) | 2.5 |
| Temazepam | 11.5 |
| Chlordiazepoxide | 17.5 |
| Medazepam | 19.0 |
| Flurazepam | 70.0 |
| Diphenyl hydantoin | 1000 |
| Amphetamine | <1000 |
| Morphine | <1000 |
| Methadone | <1000 |
| Phenobarbital | <1000 |

It is evident from the above table that with the exception of flurazepam, which differs substantially from oxazepam in having a fluorine substituent on the phenyl substituent and a large group bonded to the 1-nitrogen, antibodies are able to detect the more common benzdiazepine tranquilizing drugs. And where the drugs have been abused and relatively high levels taken, those drugs such as medazepam and librium would be detectable. Therefore, with the subject assay one is able to make a rapid screen to determine whether one or more of the more popular benzdiazepine tranquilizers has been employed. Where the particular benzdiazepine tranquilizer employed is known, a quantitive or semi-quantitative determination of the benzdiazepine can be made.

In testing various patients known to be taking Librium or Valium, at dosages of 5mg not more than 3 times in a 12 hour period, the valves obtained in the urine by the subject assays were below the 1μg/ml value which was used as a cut-off for a positive result. However, with patients receiving 15 to 50mg of the benzdiazepine drug per dose, 35 of 41 urine samples from patients known to be taking benzdiazepine drugs were shown to be positive. However no information was available as to the period of time between the taking of the drug and the taking of the urine sample.

The results show that the subject assay is effective for determining not only oxazepam, but also Valium and Librium. It should be noted that these compounds are subjected to metabolism and the production of metabolites. Therefore, Valium, Librium and Oxazepam are metabolized to form compounds which together with any unmetabolized benzdiazepine drug is capable of being detected in the subject immunoassay.

The compounds of the subject invention are particularly effective in providing reagents which are used in immunoassays for the determination of benzdiazepine drugs. Excellent reproducibility is obtained in the assay, as well as high sensitivity. In addition, the antibodies which are provided are able to detect a number of different benzdiazepine drugs in the urine as metabolites. Thus, high specificity is achieved for a narrow class of compounds, so that the subject assay can be used to provide a rapid determination of benzdiazepine usage by carrying out a simple and rapid urine analysis.

The subject benzdiazepine drugs are for the most part highly insoluble in water and difficult to conjugate. The problems of preparing appropriate polypeptide conjugates which may then be used for the production of antibodies is overcome by employing the compounds of the subject invention. The antibodies which are produced with the conjugated antigens of the subject invention are found to provide the desired high binding constants for the desired group of compounds, as well as high concentrations, so that they may be diluted to provide economic concentrations of antibodies.

Although the foregoing invention has been described in some detail by way of illustration and example for purposes of clarity of understanding, it will be obvious that certain changes and modifications may be practiced within the scope of the appended claims.

What is claimed is:

1. A compound of the formula:

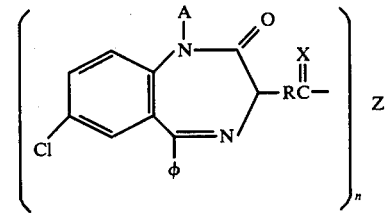

wherein:
A is hydrogen or lower alkyl of from 1 to 3 carbon atoms;
R is a linking group of from 0 to 8 carbon atoms and 0 to 4 heteroatoms which are chalcogen and nitrogen;
Z is Y, wherein Y is an antigenic poly(amino acid);
n is at least 1 and not greater than the molecular weight of Y divided by 500; and
X is chalcogen or nitrogen.

2. A compound according to claim 1, wherein n is not greater than the molecular weight of Y divided by 1,500.

3. A compound of the formula:

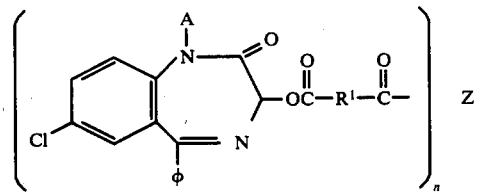

wherein:
A is hydrogen or lower alkyl of from 1 to 3 carbon atoms;
Z is an antigenic poly(amino acid);
$R^1$ is an aliphatic radical of from 1 to 6 carbon atoms having from 0 to 1 site of ethylenic unsaturation and from 0 to 1 heteroatom of atomic number 7 to 8;
n is at least 1 and not greater than the molecular weight of Z divided by 1,500.

4. A compound according to claim 3, wherein $R^1$ is polymethylene of from 2 to 4 carbon atoms.

5. A compound according to claim 3, wherein said antigenic poly(amino acid) is an albumin.
6. A compound of the formula:
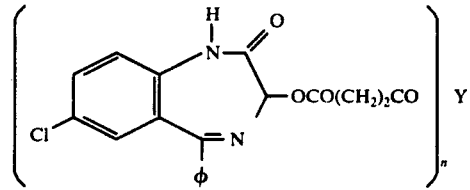
wherein:
Y is an antigenic poly(amino acid) and $n$ is at least 1 and not greater than the molecular weight of Y divided by 1,500.
* * * * *